United States Patent [19]

Holland et al.

[11] 4,260,841

[45] Apr. 7, 1981

[54] CONVERSION OF OXYGENATED PRODUCTS OF FISCHER-TROPSCH SYNTHESIS

[75] Inventors: Robert E. Holland, Mullica Hill; Samuel A. Tabak, Wenonah, both of N.J.

[73] Assignee: Mobil Oil Corporation, Fairfax, Va.

[21] Appl. No.: 72,819

[22] Filed: Sep. 4, 1979

[51] Int. Cl.³ .................... C10G 25/03; C10G 17/08; C10G 3/00
[52] U.S. Cl. ................. 585/319; 260/449 R; 260/450; 585/638; 585/407; 585/408; 585/640
[58] Field of Search .................. 208/950, 89, 92, 141, 208/187–188, 263, 297, 301, 303; 585/407, 638, 408, 640, 469, 319; 260/499 R, 450

[56] References Cited

U.S. PATENT DOCUMENTS

| | | | |
|---|---|---|---|
| 3,702,886 | 11/1972 | Argauer et al. | 208/111 X |
| 3,907,915 | 9/1975 | Chang et al. | 208/141 X |
| 3,928,483 | 12/1975 | Chang et al. | 208/135 X |
| 3,998,898 | 12/1976 | Chang et al. | 208/141 X |
| 4,148,835 | 4/1979 | Chen et al. | 585/408 X |
| 4,156,698 | 5/1979 | Dwyer et al. | 585/408 |

*Primary Examiner*—Delbert E. Gantz
*Assistant Examiner*—G. E. Schmitkons
*Attorney, Agent, or Firm*—C. A. Huggett; R. J. Cier

[57] ABSTRACT

Water-soluble oxygenates of Fischer-Tropsch synthesis separated from water and acids are sequentially upgraded by a dehydration catalyst and a special zeolite catalyst to produce gasoline, LPG and light fuel oil.

5 Claims, 1 Drawing Figure

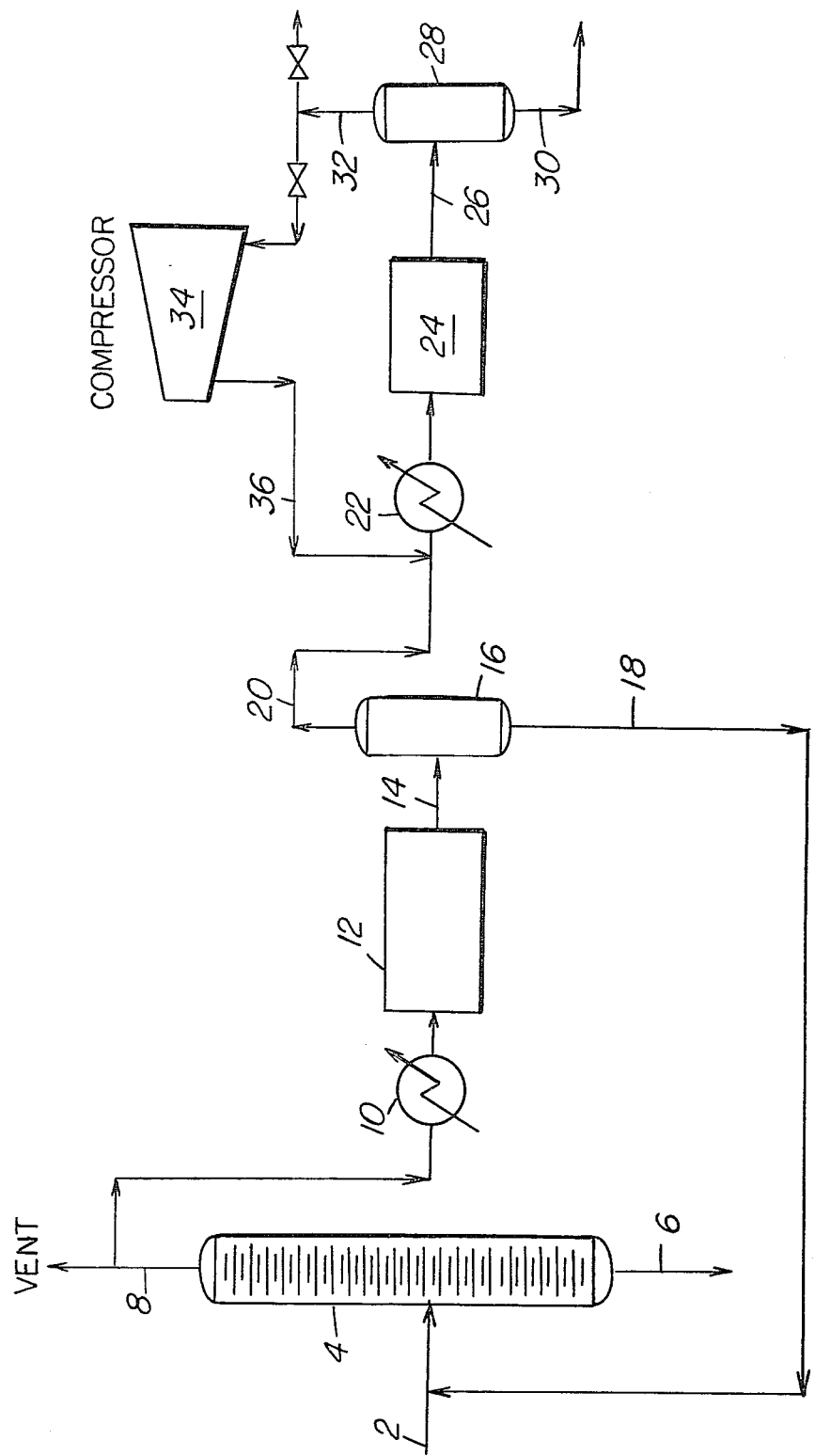

CONVERSION OF OXYGENATED PRODUCTS OF FISCHER-TROPSCH SYNTHESIS

BACKGROUND OF THE INVENTION

The conversion of oxygenated organic compounds to hydrocarbons including gasoline has been the subject of numerous prior-art disclosures. That is, U.S. Pat. No. 3,928,483 issued Dec. 23, 1975 discloses a process for the production of aromatic rich gasoline boiling range hydrocarbons from lower alcohols such as methanol, ethanol, propanol and corresponding ethers. In this patent, the process is carried out in two or more stages wherein the alcohol or ether is contacted with a condensation catalyst to produce aliphatic dehydration products and water. The dehydration product is thereafter converted to gasoline boiling hydrocarbon by contact with a special crystalline aluminosilicate zeolite providing a silica-to-alumina ratio greater than 12, a constraint index within the range of 1 to 12 and a dried crystal density of not less than about 1.6 grams per cubic centimeter. A ZSM-5 crystalline zeolite is representative of the special class of zeolite providing the above defining characteristics. U.S. Pat. No. 3,907,915 is directed to the conversion of aliphatic carbonyl containing compounds with the special zeolite above defined. U.S. Pat. No. 3,998,898 is directed to converting a mixture of a difficult to convert aliphatic organic compound in combination with easily converted aliphatic alcohols, esters, acetals and analogs thereof over the special crystalline zeolite above defined to produce highly aromatic gasoline hydrocarbons and light aliphatic hydrocarbons.

SUMMARY OF THE INVENTION

The present invention is directed to an improved method and combination of processing steps for converting a wide spectrum of oxygenated products and particularly the water soluble oxygenates obtained from a Fischer-Tropsch operation to valuable hydrocarbon products including gaseous and gasoline boiling range liquid hydrocarbons. The liquid hydrocarbons formed by the process may comprise high octane gasoline and/or good quality light or middle distillate.

The improved process of this invention generally involves collecting and passing the mixed water soluble oxygenates of a Fischer-Tropsch syngas conversion operation comprising low and higher boiling alcohols, ethers, aldehydes, ketones, acids and water, after separation of acids and some water, in contact with a dehydration catalyst under selectively restricted adiabatic temperature conditions to achieve at least 25% dehydration conversion of the feed and thereafter processing all or a part of the product of dehydration over a special crystalline aluminosilicate defined below to produce premium fuels comprising gases, high octane $C_5^+$ gasoline and/or some distillate boiling range hydrocarbons. In this combination operation, the dehydration of the charged oxygenates is important and effected under conditions to achieve an elevated conversion level normally falling short of complete conversion dehydration of the oxygenates. Thereafter a water phase and unconverted oxygenates are separated from converted material. The unconverted oxygenates and the water phase are thereafter recycled to the primary distillation zone upstream of the dehydration zone. The dehydrated oxygenates separated and substantially water free are thereafter converted by a special zeolite catalyst herein described in a separate conversion zone.

The combination process of the invention achieves significant advantages at least with respect to the zeolite catalyst life by substantially reducing the amount of water and unconverted oxygenates contacting the zeolite catalyst. The special zeolite catalytic conversion of the water-free dehydrated oxygenates is more efficient, since the necessity for quenching of the zeolite catalyst conversion operation is virtually eliminated and this gasoline-components-forming operation can thus be sustained at a more optimum higher gasoline forming temperature.

The processing combination of the invention is particularly concerned with processing $C_2^+$ oxygenates of a Fischer-Tropsch syngas conversion operation and dehydration products thereof, since conversion of such material will provide more aromatics and gasoline boiling compounds than can be derived from converting methanol. The charged $C_2^+$ oxygenate stream following dehydration will contain less water than is normally found in crude methanol and therefore any high temperature steaming of the special crystalline zeolite catalyst will be proportionately less. Thus the significant advantages of the processing combination reside in operating the gasoline component forming stage independently of the initial dehydration state, and any unconverted (undehydrated) oxygenates can be separated and recycled to the distillation operation upstream of the dehydration zone.

The crystalline aluminosilicate component used is a special crystalline zeolite such as ZSM-5 zeolite which is characterized by a pore dimension greater than about 5 Angstroms, i.e. it is capable of sorbing paraffins, it has a silica-to-alumina ratio of at least 12 and a constraint index within the range of 1 to 12. Zeolite A, for example, with a silica-to-alumina ratio of 2.0, is not useful in this invention, and it has no pore dimension greater than about 5 Angstroms.

The crystalline aluminosilicates herein referred to, also known as zeolites, constitute an unusual class of natural and synthetic minerals. They are characterized by having a rigid crystalline framework structure composed of an assembly of silicon and aluminum atoms, each surrounded by a tetrahedron of shared oxygen atoms, and a precisely defined pore structure. Exchangeable cations are present in the pores.

The zeolites utilized herein exhibit some unusual properties. They are very active even with silica-to-alumina ratios exceeding 30. This activity is surprising, since catalytic activity of zeolites is generally attributed to framework aluminum atoms and cations associated with these aluminum atoms. These zeolites retain their crystallinity for long periods in spite of the presence of steam even at high temperatures which induce irreversible collapse of the crystal framework of other zeolites, e.g. of the X and A type. Furthermore, carbonaceous deposits, when formed, may be removed by burning at higher than usual temperatures to restore activity. In many environments the zeolite of this class exhibit very low coke forming capability, conducive to very long times on stream between burning regenerations.

An important characteristic of the crystal structure of this class of zeolites is that it provides constrained access to, and egress from, the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred zeolites useful in this invention have a silica-to-alumina ratio of at least about 12 and a structure providing constrained access to the crystalline free space.

The silica-to-alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica-to-alumina ratio of at least 12 are useful, it is preferred to use zeolites having higher ratios of at least about 30. Such zeolites, after activation, acquire an intracrystalline sorption capacity for normal hexane which is greater than that for water, i.e., they exhibit "hydrophobic" properties. It is believed that this hydrophobic character is advantageous in the present invention.

The zeolites useful as catalysts in this invention freely sorb normal hexane and have a pore dimension greater than about 5 Angstroms. In addition, their structure must provide constrained access to some larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is substantially excluded and the zeolite is not of the desired type. Zeolites with windows of 10-membered rings are preferred, although excessive puckering or pore blockage may render these zeolites substantially ineffective. Zeolites with windows of 12-membered rings do not generally appear to offer sufficient constraint to produce the advantageous conversions desired in the instant invention, although structures can be conceived, due to pore blockage or other cause, that may be operative.

Rather than attempt to judge from crystal structure whether or not a zeolite possesses the necessary constrained access, a simple determination of the "constraint index" may be made by continuously passing a mixture of equal weight of normal hexane and 3-methylpentane over a small sample, approximately 1 gram or less, of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° F. and 950° F. to give an overall conversion between 10% and 60%. The mixture of hydrocarbons is passed at 1 liquid hourly space velocity (i.e., 1 volume of liquid hydrocarbon per volume of catalyst per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10}(\text{fraction of n-hexane remaining})}{\log_{10}(\text{fraction of 3-methylpentane remaining})}$$

The constraint index approximates the ratio of the cracking rate constants for the two hydrocarbons. Catalysts suitable for the present invention are those which employ a zeolite having a constraint index from 1.0 to 12.0. Constraint Index (C.I.) values for some typical zeolites, including some not within the scope of this invention, are:

| CAS | C.I. |
| --- | --- |
| Erionite | 38 |
| ZSM-5 | 8.3 |
| ZSM-11 | 8.7 |
| ZSM-35 | 6.0 |
| TMA Offretite | 3.7 |
| ZSM-38 | 2.0 |
| ZSM-12 | 2 |
| Beta | 0.6 |
| ZSM-4 | 0.5 |
| Acid Mordenite | 0.5 |
| REY | 0.4 |
| Amorphous Silica-alumina | 0.6 |

The above-described Constraint Index is an important, and even critical, definition of those zeolites which are useful to catalyze the instant process. The very nature of this parameter and the recited technique by which it is determined, however, admit of the possibility that a given zeolite can be tested under somewhat different conditions and thereby have different constraint indexes. Constraint Index seems to vary somewhat with severity of operation (conversion). Therefore, it will be appreciated that it may be possible to so select test conditions to establish multiple constraint indexes for a particular given zeolite which may be both inside and outside the above defined range of 1 to 12.

Thus, it should be understood that the parameter and property "Constraint Index" as such value is used herein is an inclusive rather than an exclusive value. That is, a zeolite when tested by any combination of conditions within the testing definition set forth hereinabove to have a constraint index of 1 to 12 is intended to be included in the instant catalyst definition regardless that the same identical zeolite tested under other defined conditions may give a constraint index value outside of 1 to 12.

The class of zeolites defined herein is exemplified by ZSM-5, ZSM-11, ZSM-12, ZSM-21, and other similar materials. Recently issued U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

U.S. application Ser. No. 358,192, filed May 7, 1973, and now abandoned, the entire contents of which are incorporated herein by reference, describes a zeolite composition, and a method of making such, designated as ZSM-21 which is useful in this invention. Recent evidence has been adduced which suggests that this composition may be composed of at least two different zeolites, designated ZSM-35 and ZSM-38, one or both of which are the effective material insofar as the catalysis of this invention is concerned. Either or all of these zeolites is considered to be within the scope of this invention. ZSM-35 is described in U.S. Pat. No. 4,016,245 (U.S. application Ser. No. 528,061, filed Nov. 29, 1974 as continuation-in-part of Ser. No. 393,767, a continuation-in-part of Ser. No. 358,192) ZSM-38 is described in U.S. application Ser. No. 528,060, filed Dec. 29, 1974, now U.S. Pat. No. 4,046,859.

The specific zeolites described, when prepared in the presence of organic cations, are substantially catalytically inactive, possibly because the intracrystalline free space is occupied by organic cations from the forming solution. They may be activated by heating in an inert atmosphere at 1000° F. for 1 hour, for example, followed by base exchange with ammonium salts, followed by calcination at 1000° F. in air. The presence of organic cations in the forming solution may not be absolutely essential to the formation of this special type zeolite; however, the presence of these cations does appear to favor the formation of this special type of zeolite. More generally, it is desirable to activate this type zeolite by base exchange with ammonium salts, followed by calcination in air at about 1000° F. for from about 15 minutes to about 24 hours.

Natural zeolites may sometimes be converted to this type zeolite by various activation procedures and other treatments such as base exchange, steaming, alumina extraction and calcination, alone or in combinations. Natural minerals which may be so treated include ferrierite, brewsterite, stilbite, dachiardite, epistilbite, heulandite and clinoptilolite. The preferred crystalline aluminosilicates are ZSM-5, ZSM-11, ZSM-12 and ZSM-21, with ZSM-5 in the acid form, i.e. H-ZSM-5, being particularly preferred.

In a preferred aspect of this invention, the initial zeolites useful as catalysts herein are selected as those having a crystal framework density, in the dry hydrogen form, of not substantially below about 1.6 grams per cubic centimeter. It has been found that zeolites which satisfy all three of these requirements are most desired. Therefore, the preferred catalysts of this invention are those comprising zeolites having a constraint index as defined above of about 1 to 12, a silica-to-alumina ratio of at least about 12 and a dried crystal density of not substantially less than about 1.6 grams per cubic centimeter. The dry density for known structures may be calculated from the number of silicon plus aluminum atoms per 1000 cubic Angstroms, as given e.g. on page 19 of the article on "Zeolite Structure" by W. M. Meier. This paper, the entire contents of which are incorporated herein by reference, is included in "Proceedings of the Conference on Molecular Sieves, London, April 1967", published by the Society of Chemical Industry, London, 1968. When the crystal structure is unknown, the crystal framework density may be determined by classical pycnometer techniques. For example, it may be determined by immersing the dry hydrogen form of the zeolite in an organic solvent which is not sorbed by the crystal. It is possible that the unusual sustained activity and stability of this class of zeolites are associated with its high crystal anionic framework density of not less than about 1.6 grams per cubic centimeter. This high density of course must be associated with a relatively small amount of free space within the crystal, which might be expected to result in more stable structures. This free space, however, seems to be important as the locus of the catalytic activity.

Crystal framework densities of some typical zeolites, including some which are not within the purview of this invention, are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

DISCUSSION OF SPECIFIC EMBODIMENTS

Table 1 below identifies a typical oxygenated product stream of a Fischer-Tropsch syngas conversion operation.

TABLE 1

Oxygenated Product of Fischer-Tropsch Synthesis

| Components | wt. % |
|---|---|
| $H_2O$ | 15.0 |
| Acetaldehyde | 2.4 |
| MEOH | 5.1 |
| ETOH | 44.3 |
| Acetone + $C_3$ Alde. | 12.2 |
| i-$C_3OH$ | 3.8 |
| 1-$C_3OH$ | 6.2 |
| MEK + $C_4$ Alde. | 4.0 |
| 2-$C_4OH$ | .5 |
| 2Me-1-$C_3OH$ | .5 |
| $C_5$ Ketones | 1.0 |
| 1-$C_4OH$ | 2.9 |
| $C_5$ Alcohols | 1.5 |
| $C_6^+$ Oxygenates | .4 |
| | 100.0 |

Table 2 below identifies the boiling points of the major oxygenated components of the charge materials and their dehydration products. It will be noted from Table 2 that at the indicated "Proposed Cut Point" the unconverted portion of the charge will separate with the water phase and the dehydration product may be separated as vaporous material from a separation zone maintained under the identified temperature and pressure conditions. This vapor/liquid separation operation is maintained independent of the initial reactor dehydrating operating conditions.

TABLE 2

Boiling Point at 100 PSIA

| | |
|---|---|
| $C_2=$ | −79.9° F. |
| $C_3=$ | 42.3 |
| Dimethyl Ether | 70.0 |
| 1-$C_4=$ | 133. |
| Acetaldehyde | 168. |
| 1-$C_5=$ | 212. |
| ------ Proposed Cut Point | |
| Propionaldehyde | 246. |
| Methanol | 252. |
| Acetone | 258. |
| Ethanol | 276 |

TABLE 2-continued

| Boiling Point at 100 PSIA | |
|---|---|
| Isopropanol | 281 |
| 1-$C_6$= | 284 |
| n-Propanol | 318 |
| Methyl Ethyl Ketone | 322 |
| Water | 328 |

Table 3 below identifies the product distribution obtained by processing the feed stream of Table 1 over the zeolite catalyst to obtain gasoline boiling components.

TABLE 3

| | Example | |
|---|---|---|
| | Start of Run | After 4 Days |
| Mass Recovery wt. % | | |
| $H_2O$ | 47.9 | 47.0 |
| CO | — | — |
| $CO_2$ | 0.1 | .2 |
| Hydrocarbons | 52.0 | 52.8 |
| Hydrocarbon Product Distribution wt. % | | |
| $C_1$ | — | 0.1 |
| $C_2$ | 0.5 | 0.7 |
| $C_3$ | 8.5 | 5.0 |
| $C_4$ | 14.1 | 11.8 |
| $C_5$ | 11.6 | 13.2 |
| $C_6$+Paraffins, Olefin, Naphthenes | 16.2 | 31.1 |
| Benzene | 0.4 | 0.7 |
| Toluene | 7.4 | 4.0 |
| Ethylbenzene | 2.6 | 1.4 |
| Xylenes | 12.3 | 7.2 |
| $C_9$ Aromatics | 15.0 | 13.4 |
| $C_{10}$ Aromatics | 6.9 | 7.4 |
| $C_{11}$ Aromatics | 3.1 | 2.9 |
| Naphthalenes | .2 | .2 |
| Unknown Hydrocarbons | 1.2 | 0.9 |
| | 100.0 | 100.0 |
| $C_5$+wt. % | 76.9 | 82.4 |
| $C_5$+R + 0 | 98.7 | 97.7 |
| $C_6$+R + 0 | 101.3 | 99.1 |

The drawing is a schematic showing of the processing arrangement of this invention comprising a primary distillation zone, a dehydration zone, a dehydrated product separation zone, a crystalline conversion zone and a product separation zone.

Referring now to the drawing by way of example, a stream of oxygenated products and water separated from the product of a Fischer-Tropsch syngas conversion operation is charged to the process of this invention by conduit 2 to a distillation column or zone 4 maintained at a temperature and a pressure selected to achieve separation of water and acids from the remaining oxygenates. In distillation zone 4, a separation is made in the presence of relatively large amounts of water, a water phase and acids withdrawn from the bottom of the zone by conduit 6, with the remaining oxygenates and water being recovered from the top thereof by conduit 8. The oxygenates and water in conduit 8 are heated in heat exchanger 10 to an elevated temperature within the range of 600° to 1100° F. and preferably about 900° F. before being passed in contact with a dehydrating catalyst in zone 12. A portion of the material in conduit 8 may be passed to vent as shown when required. In dehydrating zone 12, the oxygenates and retained water in conduit 8 are passed in contact with a dehydration catalyst suitable for the purpose. Several different dehydrating catalysts have been identified in the prior art, but it is preferred to employ gamma alumina for this purpose. Dehydration zone 12 is maintained under temperature conditions which will achieve a high conversion of the oxygenates to a dehydrated product suitable for passing upon recovery in contact with the gasoline forming special zeolite catalyst. Table 4 below identifies conditions which may be employed to achieve a desired conversion of dehydrated oxygenates preferably to within the range of 25 to 100%.

TABLE 4

ENDOTHERMIC HEATS OF DEHYDRATION AT 700° F.

ROH ---> R= + $H_2O$

| Alcohol | —H Kcal/Mole | —H cal/gm |
|---|---|---|
| Ethanol | 11.20 | 243 |
| n-Propanol | 8.93 | 149 |
| i-Propanol | 12.15 | 203 |
| n-Butanol[1] | 5.37 | 72 |
| n-Pentanol[2] | 4.19 | 48 |
| n-Hexanol[3] | 4.31 | 42 |

[1]Olefin product taken as t-2-butene
[2]Olefin product taken as 2M-2-butene
[3]Olefin product taken as 2M-2-pentene

ESTIMATED ADIABATIC TEMPERATURE DROP FOR 900° F. INLET

| Charge Composition | Mole % | Conversion % | $T$Adiabatic °F. |
|---|---|---|---|
| Ethanol | 84.3 | | |
| n-Propanol | 8.3 | 100 | 420 |
| i-Propanol | 3.0 * | 50 | 575 |
| n-Butanol | 3.4 | 25 | 745 |
| n-Pentanol | 1.0 | | |

$T$Adiabatic = 700° F. at 31% conversion
*Charge composition of each conversion level The product of the dehydration operation and comprising dehydrated oxygenates, water and unconverted oxygenates (not dehydrated) is passed by conduit 14 to a separation zone 16 maintained at a selected temperature and pressure designed to achieve a separation of dehydration product commensurate with a separation shown, for example, by Table 2 above. Thus a separation is made in zone 16 under selected temperature and pressure conditions which will achieve the recovery of water and unconverted oxygenates withdrawn by conduit 18 for recycle to the distillation zone 4. Separation of water from unconverted oxygenates before recycle is not essential. Light olefins and other dehydration products such as herein identified are recovered from separation zone 16 by conduit 20 for passage to heater 22 wherein the temperature of the light olefin stream is raised before contacting the special zeolite catalyst herein identified in zone 24. In zone 24, the temperature is maintained within the range of 400° to 900° F. and a pressure within the range of atmospheric to 1000 psig. In this special zeolite catalyst contacting operation, the light olefins and other products of dehydration are converted to premium fuel products of high octane value including $C_4$ to $C_{10}$ olefin and aromatic boiling components and of product selectivity such as defined in Table 3 above. However, by using the combination of relatively low temperatures and high pressures, the product selectivity may be altered to improve the yield of middle distillate.

The product of the zeolite catalyst conversion step is passed by conduit 26 from zone 24 to a separator zone 28 wherein a separation is made in one embodiment to recover $C_5$+ gasoline product of about 98 R+0 octane which is withdrawn by conduit 30. Primarily $C_4$ and lower boiling material is withdrawn by conduit 32.

All or a portion of the separated $C_4$ and lower boiling material may be recovered for further treatment in downstream equipment not shown. For example, a portion of this material after separation in appropriate equipment may be used as feed to an alkylation zone, a polymerization zone or a combination thereof. On the other hand, a portion of this material may be used to provide LPG or a fuel gas used to provide the heat requirements of the process.

In yet another embodiment, it is contemplated passing all of the $C_4$ and lighter material through a compression zone 34 to raise the pressure therein sufficient for recycle by conduit 36 and admixture with the dehydrated feed in conduit 20 charged to heater 22. Recycle of the $C_4$ and lower boiling hydrocarbons recovered as above discussed is intended to take advantage of the restructuring characteristics of the special zeolite to produce longer chain olefins and/or aromatics, depending upon the particular combination of temperature and pressure operating conditions selected.

Having thus generally described the method and processing combination of this invention and provided specific examples in support thereof, it is to be understood that no undue restrictions are to be imposed by reason thereof except as defined by the following claims.

We claim:

1. A process for upgrading a mixture of $C_2$ plus water soluble oxygenates comprising primarily a mixture of $C_5$ and lower boiling alcohols, aldehydes, ketones and water which comprises, distilling the $C_2$ plus water soluble oxygenates to remove water and acids from a mixture of $C_5$ and lower boiling alcohols, aldehydes and ketones, dehydrating the mixture of $C_5$ and lower boiling alcohols, aldehydes and ketones under conditions to achieve within the range of 25 to 100% conversion thereof to a dehydrated product, separating a dehydrated product from water and unconverted material, recycling the separated water and unconverted material to the distillation step, passing the dehydrated product in contact with a special zeolite catalyst characterized by a pore opening of at least 5 Angstroms, a silica-to-alumina ratio of at least 12 and a constraint index within the range of 1 to 12, said contact between said dehydrated product and said zeolite catalyst being effected at a temperature within the range of 400° to 900° F. and a pressure sufficient to produce a product comprising high octane gasoline boiling components and aromatics.

2. The process of claim 1 wherein the product of said zeolite catalyst operation is separated to provide a $C_4$ and lower boiling product from a higher boiling product and separated lower boiling product is recycled to the zeolite catalyst conversion operation.

3. The process of claim 2 wherein separated lower boiling product is used to provide LPG and fuel for the process.

4. A method for upgrading the water soluble oxygenates of a Fischer-Tropsch syngas conversion operation which comprises, passing water soluble oxygenates comprising alcohols, aldehydes and ketones separated from a water phase by distillation in contact with a dehydration catalyst under conditions to obtain a dehydrated product, passing the dehydrated product in contact with a zeolite catalyst providing a pore opening of at least 5 Angstroms, a silica-alumina ratio of at least 12 and a constraint index within the range of 1 to 12 and maintaining the temperature and pressure conditions selective for the production of primarily gasoline boiling range component of high octane alone or in combination with producing a middle distillate boiling material.

5. The method of claim 4 wherein the dehydration catalyst is gamma alumina and the zeolite catalyst is ZSM-5.

* * * * *